United States Patent [19]

Taylor

[11] 4,026,152

[45] May 31, 1977

[54] AUTOMATIC SAMPLING APPARATUS

[76] Inventor: Murland L. Taylor, 5300 Main, Parsons, Kans. 67357

[22] Filed: Feb. 5, 1976

[21] Appl. No.: 655,528

[52] U.S. Cl. .............................. 73/421 R; 73/423 R
[51] Int. Cl.² ......................................... G01N 1/10
[58] Field of Search .......... 73/422 R, 423 R, 421 R

[56] References Cited

UNITED STATES PATENTS

| | | | |
|---|---|---|---|
| 2,968,948 | 1/1961 | Rose | 73/421 R |
| 3,751,991 | 8/1973 | Fisher et al. | 73/421 R |
| 3,802,270 | 4/1974 | Daniels et al. | 73/422 R |

*Primary Examiner*—Donald O. Woodiel
*Attorney, Agent, or Firm*—Robert E. Breidenthal

[57] ABSTRACT

A sampling probe is associated with the delivery chute for a flowable material for cyclically removing uniformly sized discrete samples and placing the samples in a sample collector, with each removal being effected upon the delivery of a predetermined quantity of material from the chute. The probe is pneumatically actuated to isolate and remove each sample and a stepping relay is provided to count a predetermined number of unit quantities of material delivered and on completion of each such count to control the initiation of a pneumatic operation of the sampling probe.

9 Claims, 5 Drawing Figures

AUTOMATIC SAMPLING APPARATUS

The present invention relates to new and useful improvements in apparatus for collecting samples of a material on a representative basis for such purposes as monitoring quality control, sequestering lot samples for future reference, compliance with marketing codes or other governmental regulations. More specifically, the present invention has to do with the collection of a plurality of discrete and uniformly sized samples or specimens of a flowable solid material commonly bagged or containerized materials, with each specimen being collected from a dispensing chute adjacent to the discharge end thereof upon the dispensing of a predetermined quantity of the material.

An appreciation of background prior art and of proposals heretofore made can be obtained on consideration of the following United States patents which were located during a patentability search:

| | | |
|---|---|---|
| 1,966,712 | Fisher et al | July 17, 1934 |
| 2,968,948 | Rose | Jan. 24, 1961 |
| 3,229,525 | Calhoun, Jr., et al | Jan. 18, 1966 |
| 3,541,860 | George | Nov. 24, 1970 |
| 3,583,228 | Tobiassen | June 8, 1971 |
| 3,751,991 | Fisher et al | Aug. 14, 1973 |
| 3,847,023 | Mallander et al | Nov. 12, 1974 |
| 3,858,449 | Singer | Jan. 7, 1975 |

An important object of the present invention is to provide apparatus that will respond on each occurrence of a predetermined number of material measuring or metering events (such as the filling of a container, the reciprocation or rotation of material flow actuated or sensing equipment) to collect a specimen or sample of a predetermined size.

Another important object of the invention in accordance with the above object is to provide apparatus for enabling the number of predetermined events to be selectable.

Yet another important object is to provide a sampling probe that will positively obtain a specimen or sample from a material delivery conduit adjacent the delivery end and at a position within the latter wherein the rate of material flow is relatively high.

Broadly, the invention has to do with apparatus for cyclically removing samples of a flowable solid material from a dispensing conduit thereof, comprising a sample means operative on each instance of actuation thereof to withdraw a sample of material from the conduit adjacent an outlet of the latter and to place the same in a sample collector, means for measuring unit quantities of dispensed material, means for counting the number of dispensed unit quantities, means operative upon each instance of the count made by the last recited means reaching a predetermined integer to actuate the sample collecting means, and means for preselecting the value of the integer.

The invention also involves, for use in apparatus for sampling a flowable solid, a sampling probe comprising a tubular member having one end connected to a downwardly inclined collector tube and said tubular member having an open second end with mounting means being provided adapted to project the tubular member through a conduit so as to expose the second end of the tubular member to the flow of a solid flowing through the latter, a cup-shaped closure cap mounted for reciprocating motion in alignment with the second end of the tubular member between a first position embracing and closing the open second end of the tubular member and a second position spaced from the tubular member, the arrangement being such that a cycle of reciprocation of the cap sequentially opens the second end of the tubular member and then forces a predetermined volume of ambient solid material into the second end of the tubular member while closing the latter, and means for actuating a cycle of reciprocation of the cap.

Though the invention is applicable to association with metering apparatus of any delivery system such that only ordinary skill would be involved so as to cause an electric switch to be actuated once every time a given quantity of material passes through the chute, the invention has specially advantageous applicability to sampling material from a chute delivering to automatic packaging or bagging equipment. Such specially advantageous applicability resides in the fact that the present invention can be operated to collect a uniformly sized specimen upon the filling of each bag or upon any selectable number of bags being filled, it being understood that bags are filled with equal quantities of material. Therefore each collected specimen or sample can be associated with a particular filled bag or a particular group of filled bags.

When the apparatus is applied to sample a bulk of delivered material, rather than a uniformly containerized output, cyclically collected specimens collectively constitute an excellent statistical sampling of the total delivered bulk of material, it being understood that each specimen taking cycle is initiated on the sensing of the delivery of a predetermined quantity of material, such as may be sensed by rotation of a metering wheel as will be understood by those conversant with the metering art.

The invention, its operation, its applicability to various other metering systems, and various other advantages will be best appreciated in the light of the following description of a preferred embodiment thereof as applied to the metering inherent in uniformly bagging a material, such description being given in conjunction with the accompanying drawings illustrative thereof, wherein:

FIG. 1 is a broken isometric view showing in one portion the sample withdrawal structure mounted on a material delivery chute, with a portion of the latter broken away to show the probe, and with alternative positions of the withdrawal structure and of the probe cap being shown in dashed outline; and showing in the other portion the sample collection box with hidden parts of the latter being shown in dashed outline;

Figure 1:
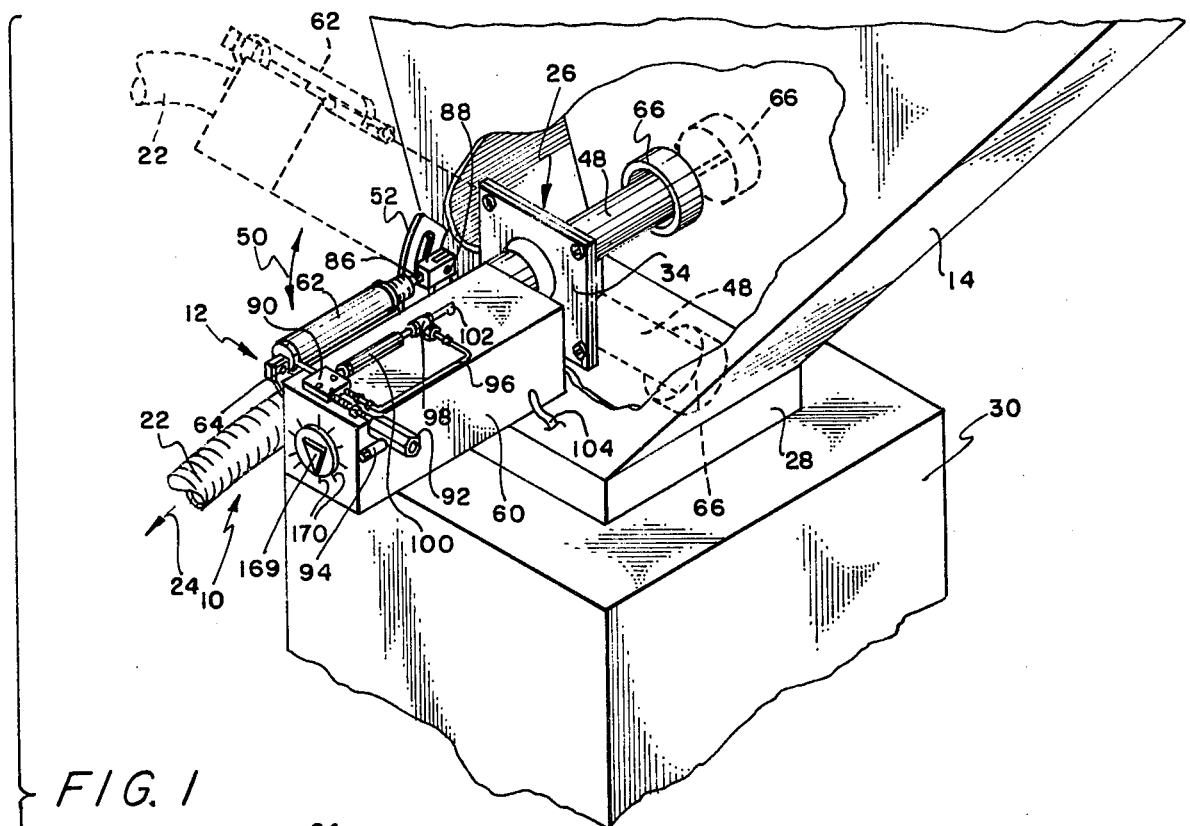
Figure 1:
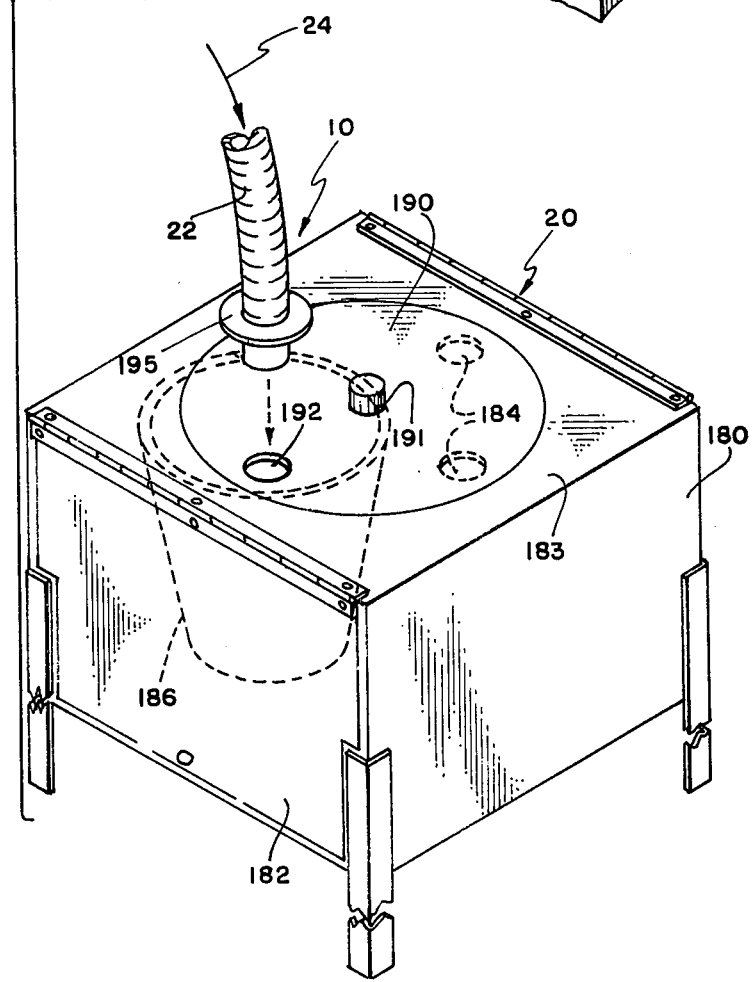
Figure 2:
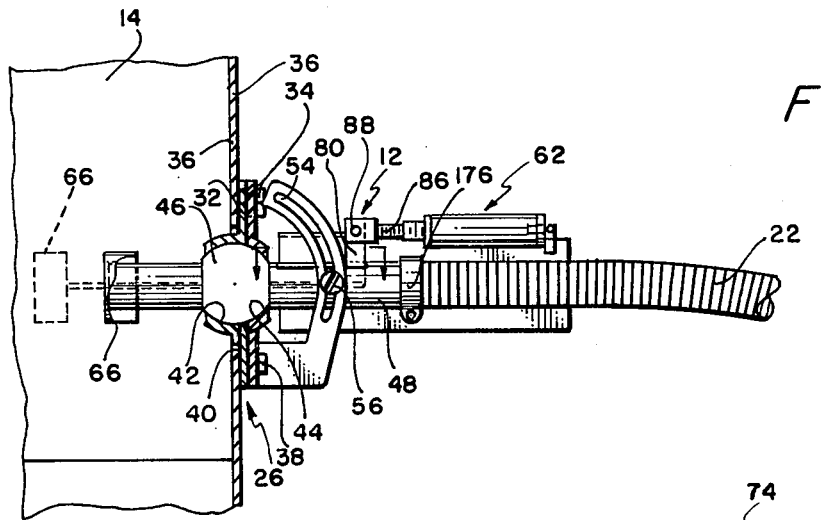
FIG. 2 is a side elevational view of the withdrawal structure of FIG. 1 with a part of the mounting means and the conduit being shown in section to better illustrate how angular adjustment of the probe is effected, and also showing alternate positions and hidden parts of the probe in dashed outline.
Figure 3:
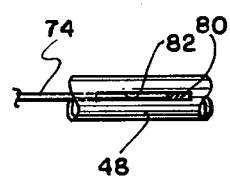
FIG. 3 is an enlarged detail view, partially in section, taken upon the plane of the section line 3—3 in FIG. 2.
Figure 4:
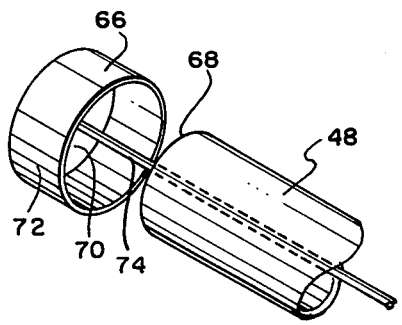
FIG. 4 is an enlarged fragmentary detail view of the sample probe with a hidden part of the actuation rod being shown in dashed outline; and, FIG. 5 is an electrical schematic of diagrammatic character illustrating the control of the sampling system.

Referring now to the drawings, wherein like numerals designate like parts throughout the various views, the numeral 10 designates the sampling system generally, such system comprising a pneumatically powered means 12 for withdrawing a sample from a dispensing chute 14 under the control of an electrical system designated generally at 16 that includes an air valve 18. The system 10 also includes a sample collecting means designated generally at 20 that receives samples withdrawn by the means 12 via flexible tubing 22 as indicated by the arrows 24 shown in connection with the two portions of FIG. 1.

The sample withdrawal means 12 is mounted by means 26 on the conduit or chute 14 adjacent the discharge end 28 of the latter, it being understood that the chute 14 gravitationally delivers under the control of any suitable valve means disposed therebelow, now shown, a flowable solid, also not shown, to an automatic bagging machine of conventional character that is partially shown at 30. Such flowable solid can be in the nature of most, if not all, of the various kinds of solid materials susceptible to bagging by automatic bagging machines.

The means 26 comprises a pair of plates 32 and 34 secured to a wall 36 of the chute 14 by fastening means 38 about an opening 40 in the wall 36.

The plates 32 and 34 in their central portions are formed with concaved sections 42 and 44 that jointly engage in a sealing and sliding fit a generally spherical or convex enlargement 46 on the exterior of and intermediate the ends of a tubular probe member 48. The arrangement is such that the tubular member 48 sealingly projects into the chute 14 and can be swung through a vertical angle above and below the horizontal as indicated by the arrow 50 in FIG. 1. The probe member 48 is secured in angularly adjusted position by means of a bracket 52 attached to the chute 14 by the fastener 38, such fastener having an arcuate slot 54 that receives therethrough a clamping screw 56 that is threaded into an enlargement or boss (not shown) on the exterior of the probe member 48. As will be understood, the probe member 48 is retained in angularly adjusted position when the clamping screw 56 is tightened.

A housing 60 is fixedly secured to the side of the tubular member 48 on the side thereof opposite the bracket 52 and an elongated pneumatically operated means 62 is mounted at 64 on the exterior of the housing 60 in fixed parallelism to and above the tubular probe member 48. The means 62 is operatively coupled to a cup-shaped cap 66 in an arrangement for reciprocating the latter between a position shown in full line in FIG. 1 closing the open end 68 of the tubular probe 48 and a position shown in dashed outline in FIG. 1 that is axially displaced from the end 68. The cap 66 comprises a closure wall 70 that is sealingly seatable against the end 68 and an integral annular skirt or flange 72 of greater diameter than the tubular probe member 48. The operative connection of the cap 66 to the means 62 comprises an elongated rod 74 fixed at one end to the wall 70 of the cap 66 and having a lateral extension 80 at its other end that projects radially outward through a longitudinal slot 82 in the top of the tubular member 48. The arrangement is such that reciprocating motion of the rod 74 effects the aforementioned reciprocation of the cap 66. The means 62 includes a piston rod 86 having a free end coupled to the lateral extension 80 by means of a clevis 88.

The pneumatic means 62 is of conventional character, as are all the hereinafter described parts of the pneumatic system, and is such that the piston rod 86 is resiliently biased to its retracted position which corresponds to the cap 66 closing the probe end 68.

A three-way air valve 90 normally connects the means 62 to an exhaust means 92 having a manually adjustable exhaust rate control 94, such valve 90 being actuable to communicate the means 62 with an air line 96.

The line 96 is connected by way of a T fitting 98 with a conventional air relay timer 100 and an air line 102; the air line 102 being respectively connected to an exhaust line 103 and a source of regulated high pressure air (not shown) by an air line 104 by the conventional three-way solenoid operated valve 18 when the latter is deenergized and energized.

The air relay timer 100 is conventional and is operatively coupled to the three-way valve 90 in such a manner as to actuate the means 62 to communicate with the air line 96 for a preselected time interval on the application of air pressure thereto from the line 102 and then to close such communication while restoring normal communication of the spring biased air cylinder or means 62 with the exhaust means 92.

Inasmuch as the line 96 is pressurized concurrently with the line 102 upon opening of the valve 18, the energization of the valve 18 to open the latter serves to introduce pressurized air into the means 62 to extend the rod 86 and open the cap with the air relay timer serving after a predetermined time thereafter to return the three-way valve 90 to normal position whereupon the cap 66 is returned by the internal resilient bias of the means 62 to its normal position at a rate determined by the setting of the manual exhaust control.

Figure 5:
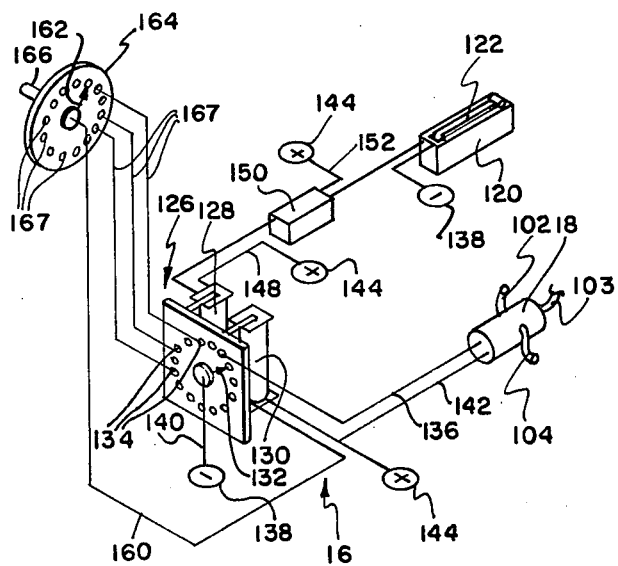

Passing now to the electrical control system 16 for effecting appropriate electrical energization of the solenoid air valve 18, attention is directed to FIG. 5, wherein the reference numeral 120 designates a normally open electric switch. The electric switch 120 includes an external actuating element 122 that is disposed to be actuated each time a unit of material is dispensed from the chute 14. In the preferred embodiment of the invention, the automatic bagging machine 30 includes means not shown for weighing a bag as it is filled to a predetermined weight and it is to be understood by those skilled in the art that the element 122 of the switch 120 is disposed in the path of a movable part of the weighing mechanism of the bagging machine. Such arrangement is not specifically illustrated as it would tend to obfuscate the actual invention. The operative association of scaling means with an electric switch arranged to be actuated once on scaling a selected value is widespread and very well known.

A resettable type of stepping relay 126 is provided that includes a stepping coil 128 and a reset coil 130, and the operation is such that the wiper or movable contact 132 moves from its illustrated reset or zero position to move stepwise in an anticlockwise direction under the control of the stepping coil 128 to sequentially contact a sequence of fixed contacts 134, with the first of such sequentially contacted fixed contacts being connected by lead 136 to the solenoid of the valve 18. The wiper arm 132 is connected to one polarity 138 of a power source (not shown) by a lead 140 and the other terminal of the solenoid of the valve 18 is connected by a lead 144 to the opposing polarity of power source. Terminals of corresponding polarities of the power source are also designated by the reference numerals 138 and 144 and are respectively symbolized by the use of minus and plus symbols, though the power source can be either of direct or alternating current.

As thus far described it will be evident that the valve 18 will be electrically energized on the relay being stepped one step from its illustrated zero or reset position.

Means is provided to energize the stepping coil 128 for a predetermined time interval on each instance of closure of the switch 120, such interval being of lesser duration than the period that the switch 120 is normally closed. Such means includes the stepping coil 128 having connections to the power source 144 via a lead 148 and via a conventional electric timer relay 150 having a normally closed switch. The relay 150 is connected to the power source 144 via a lead 152 in an arrangement such as to open the normally closed switch connection therein between the stepping coil 128 and the switch 120 a short time after closure of the latter.

It will be seen that each sequential closure of the switch 120 energizes the stepping coil 128 for sufficient time to effect a step with the period of coil energization being limited by the relay 150, whereby burn out of coil 128 is avoided.

The reset coil 130 has one terminal connected to the power source 144 and its other terminal connected via lead 160 to the movable arm 162 of a manually operable rotary selector switch 164 having an operating shaft 166. The rotary arm or movable contact 162 is operatively associated with a set of fixed contacts or terminals 167 that correspond in number to the contacts of the relay 126 engageable by the arm. Each of the contacts 134 is connected to one of the contacts 167 of the rotary switch 164 on a one-to-one basis. A representative portion of such connections are indicated by the leads 168 in FIG. 5. The zero position contact of the relay 126 is not connected to the switch 164. It will be noted that the contacts 134 and 167 are paired in their connections in sequential order.

Excepting the switch 120, the structure shown in FIG. 5 is disposed in the housing 60. The switch shaft 166 extends from the housing 60 and has an indicator knob 169 fixed thereon that can be read against indicia 170 on the housing 60 to indicate which of the terminals or contacts 167 is engaged by the movable arm 162 of the switch 164.

Upon the relay arm 132 moving to contact the contact or terminal also connected by preselection to the arm 162, a circuit is completed to energize the reset coil 130 and return the arm to its illustrated position. The reset action is such as to rotate the arm 132 clockwise to its zero position, it being noted that the energization of the valve 18 is too brief to operate the same.

From the foregoing it will be seen on assuming the initial stepping relay 126 condition shown, successive closures of the switch 120 effects a series of stepping actions with the first stepping action energizing the value 18 so as to actuate a sample taking cycle of the means 12. Such sequential stepping actions will continue until the arms 132 and 162 are electrically connected by one of the leads 168, whereupon the stepping relay 126 is reset so that the next closure of the switch 120 results in energization of the valve 18. Such electrical connection of the arms 132 and 162 can coincide with the initial stepping step from the reset position (in which event each closure of the switch 120 results in withdrawal of a sample) or be caused only after a selected number of steps thereafter. Such selection is, of course, effected by setting the switch knob 168.

Referring again to the sample withdrawing means 12, it will be seen that the probe end 68 is disposed well within the chute 14 so as to be exposed to substantial material movement. On a sampling cycle being initiated by opening of the valve 18, the cap 66 opens and moves from the tube a fixed interval and thereafter forcefully returns to its initial position at a velocity selected to be such that a desired quantity of material is forced into the probe 48. The quantity or mass of material forced into the tube on each cycle of operation is essentially predetermined by the geometry of the system, the character of the material and the rate of retraction of the cap 66. The latter is selectively controlled by the exhaust rate control 94. The angular adjustability of the probe member 48 enables a variation of the geometry to facilitate adjustment of sample weight and consistency. It has been found that such adjustability makes for more ready accommodation of a wide range of material. For example, an upward inclination of 45° might work best with some materials, while a more horizontal attitude will be preferable with others.

Material entering the probe member 48 as described above is forced into or gravitationally enters the flexible tube 22 that is fastened about the end of the probe member opposite the cap 66 as indicated at 176.

The collector comprises a cabinet 180 having a normally closed side access door 182. The top 183 of the housing has a plurality of circumferentially spaced openings 184, each of which overlies individual containers removably disposed in the housing 180; one of such containers being indicated in dashed outline at 186.

A circular selector plate 190 is rotatably mounted on the top of the housing 180 by suitable means 191 and such plate 190 has a single opening 192 therethrough that may be rotated to selectively register with any one of the openings 184.

The discharge end 194 of the flexible metal tube 22 can be inserted, to an extent limited by a stop flange 195, through the opening 192 and the selected opening 184 in registry with the latter to deposit the sample in the container 186 associated with the selected opening 184.

Attention is now invited to the appended claims in order to ascertain the actual scope of the invention.

I claim:

1. For use in apparatus for sampling a flowable solid, a sampling probe comprising a tubular member having one end connected to a downwardly inclined collector tube and said tubular member having an open second end with mounting means being provided adapted to project the tubular member through a conduit so as to expose the second end of the tubular member to the flow of a solid flowing through the latter, a closure cap mounted for reciprocating motion in axial alignment with the second end of the tubular member between a first position closing the open second end of the tubular member and a second position axially spaced from the tubular member, the arrangement being such that a cycle of reciprocation of the cap sequentially opens the second end of the tubular member and then forces ambient solid material into the second end of the tubular member while closing the latter, and means for actuating a cycle of reciprocation of the cap.

2. The combination of claim 1, wherein said means for actuating the cap comprises an actuating rod disposed within the tubular member and having one end secured to the cap and its other end operatively coupled to pneumatic means inclusive of an air relay timer for sequentially forcing the rod to move the cap from its first to its second position and thence to return the cap to its first position at a predetermined rate.

3. The combination of claim 1, wherein said means for actuating the cap is pneumatic and includes a means for selectively predetermining the rate of movement of the cap from its second to its first position.

4. The combination of claim 3, wherein said pneumatic means includes an actuating rod disposed for axial movement within the tubular member and attached to said cap.

5. The combination of claim 4, wherein said cap is cup-shaped and includes an annular skirt that embraces the tubular member in radially spaced relation when the cap is in its first position.

6. The combination of claim 2, wherein said cap is cup-shaped and includes an annular skirt that embraces the tubular member in radially spaced relation when the cap is in its first position.

7. The combination of claim 1, wherein said mounting means includes a plate adapted to constitute a portion of a material conduit with said tubular member sealingly extending through said plate.

8. The combination of claim 7, wherein means are provided to enable the tubular member to be moved angularly relative to the plate, and means for releasably securing the tubular member in selected angular relation to the plate.

9. Apparatus for cyclically removing samples of a flowable solid material from a dispensing conduit thereof, comprising a sample collecting means operative on each instance of actuation thereof to withdraw a sample of material from the conduit adjacent an outlet of the latter and to place the same in a sample collector, means for measuring unit quantities of dispensed material, means for counting the number of dispensed unit quantities, means operative upon each instance of the count made by the last recited means reaching a predetermined integer to actuate the sample collecting means, and means for preselecting the value of the integer, said sample collecting means comprising a tubular member having an open end projecting into the dispensing conduit, a cup-shaped closure cap mounted for reciprocating motion in axial alignment with the open end of the tubular member between a first position embracing and closing said open end of the tubular member and a second position axially spaced from the tubular member, the arrangement being such that a cycle of reciprocation of the cap sequentially opens the open end of the tubular member and then forces ambient solid material into the open end of the tubular member while closing the latter.

* * * * *